United States Patent [19]

Martin

[11] Patent Number: 4,844,104
[45] Date of Patent: Jul. 4, 1989

[54] DENTAL FLOSS DISPENSER

[76] Inventor: James Martin, #11, 6 Fairknowe Drive, Brockville, Ontario, Canada, K6V 1J5

[21] Appl. No.: 211,440
[22] Filed: Jun. 24, 1988
[51] Int. Cl.[4] .............................................. A61C 15/00
[52] U.S. Cl. .................................................... 132/321
[58] Field of Search ......................... 132/321, 323, 324

[56] References Cited

U.S. PATENT DOCUMENTS 4,286,611 9/1981 Talbot .................................. 132/321
4,330,014 5/1982 Glass .................................... 132/321

Primary Examiner—Robert Peshock

[57] ABSTRACT

A dental floss dispenser that includes a body having a cavity for holding a spool of the dental floss and a cover removably mounted on the body providing access to the cavity. There is an outlet hole in the body member for pulling therethrough the string of the dental floss. There are a series of side-by-side slots in walls of the body that extend across the top wall and a longitudinal cutting edge on a knife located within the body is exposed in respective ones of the slots.

6 Claims, 1 Drawing Sheet

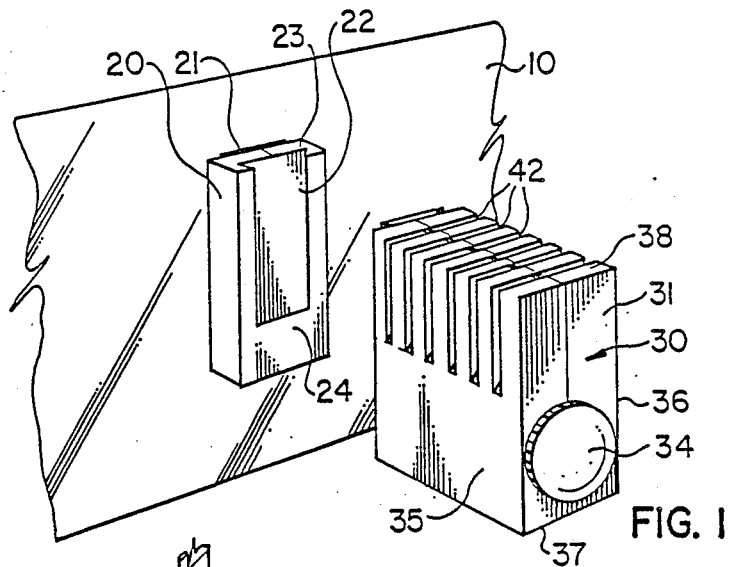
FIG. 1
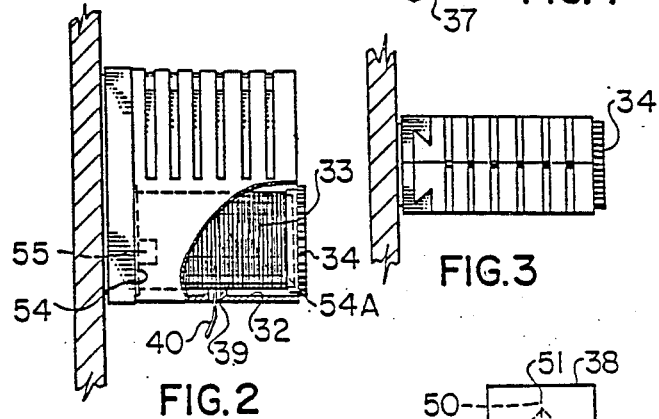
FIG. 2
FIG. 3
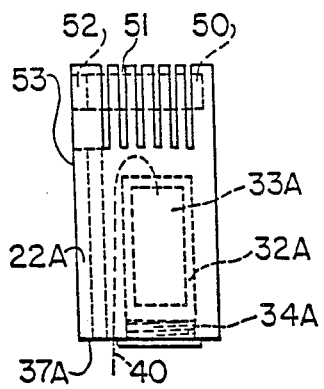
FIG. 4
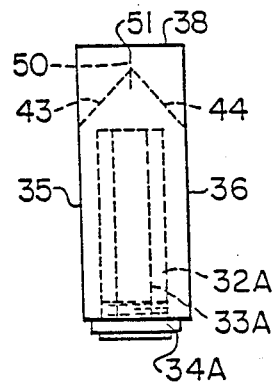
FIG. 5

DENTAL FLOSS DISPENSER

FIELD OF THE INVENTION

This invention relates to a holder for a spool of dental floss thread, cord or the like, detachably mountable on a structure, such as a bathroom mirror or wall, and including a plurality of separate and distinct areas for cutting a length from the spool.

BACKGROUND OF INVENTION

Cord and floss dispenser with cutters are well-known and by way of example, attention is directed to U.S. Pat. No. 2,929,541 issued Mar. 22, 1960 to C. Castelli et al; U.S. Pat. No. 3,480,190 issued Nov. 25, 1969 to H. Freedman and U.S. Pat. No. 2,653,776 issued Sept. 29, 1953 to A. J. Rochow. Of these, perhaps the U.S. Pat. No. 2,653,776 is of most interest with respect to the present invention in that it discloses a container for holding a ball of twine, an aperture in the container for dispensing the twine and a separate compartment that retains a razor blade and exposes the cutting edge thereof in two different locations for use in cutting the twine. The present invention has similar characteristics, but is of simplified construction and has more conveniently disposed cutting means. There is particularly provided in accordance with the present invention a dispenser comprising a body having a cavity for holding a spool of dental floss, string, thread or the like; a cover removably mounted on said body providing access to the cavity for replacing a spent spool of said dental floss or the like; an outlet hole in the body member for pulling therethrough a string of dental floss wound on a spool in the cavity; a series of side-by-side slots in a wall of the body; and a blade located within said body and having a longitudinal cutting edge exposed in respective ones of said slots. In the preferred form the side-by-side slots have a bottom wall that slopes upwardly and inwardly toward one another from respective opposite sides of the dispenser body meeting at an apex located below a top wall of the body and wherein the cutting blade projects from such apex exposing a cutting edge below the top wall of the body.

LIST OF DRAWINGS

The invention is illustrated by way of example in the accompanying drawings wherein:

FIG. 1 is an oblique view of a dental floss dispenser provided in accordance with the present invention along with a mounting bracket therefore and wherein such members are shown in a disassembled state;

FIG. 2 is a side elevational, partial sectional, view of the dispenser and mounting bracket shown in FIG. 1 in an assembled state and mounted on the face of a mirror;

FIG. 3 is a top plan view of FIG. 2;

FIG. 4 is a side elevational view, illustrating a minor modification; and

FIG. 5 is a right hand end elevational view of FIG. 4.

DESCRIPTION OF PREFERRED EMBODIMENT

Referring to the drawings, there is illustrated a portion of a mirror 10 having a mounting bracket 20 attached thereto as by double-faced tape 21 and which removably receives a dental floss dispenser 30. The mounting bracket 20 has a dove tail groove 22 in the front face thereof and which is open at the upper end designated 23 and closed at the lower end as indicated at 24.

The floss dispenser 30 comprises a rectangular body 31 with a cavity 32 therein for receiving a spool of dental floss 33. A cap or cover 34 frictionally fits or threads into an aperture in a wall of the body at the end of the cavity providing access to the cavity for replacement of spent spools of dental floss.

The body is generally rectangular with respective opposite side faces 35 and 36, a bottom wall 37 and a top wall 38. The bottom wall 37 is provided with an aperture 39 for dispensing therethrough a thread of dental floss 40 from the spool 33.

In a portion of the side walls, and across the top wall, there are a plurality of side-by-side grooves 42, each having bottom wall portions 43 and 44 sloping upwardly and inwardly toward one another from the respective opposite side walls 35 and 36 toward the top wall 38. The walls 43 and 44 meet at an apex spaced downwardly from the top wall 38. The body 31 is preferably molded of a plastics material and has embedded therein a rectangular blade 50 with a longitudinal cutting edge 51. The cutting edge 51 is spaced downwardly from the top wall 38 and thus, is not accessible even by infant's fingers thereby making the same safely usable in any household bathroom or other facility. The razor blade type cutter 50 is either embedded as in the embodiments of 1 and 2 at the time of molding of the body 31 or, as in the embodiment of FIG. 4, is insertable into a cavity in the body through a slot 52 in the back end wall 53 of the body.

In the embodiment illustrated in FIG. 1, the cavity for the spool of dental floss is horizontal and the far end of the cavity has a recess defined by an outstanding annular flange 54 that receives an end portion of the spool journaling such end for rotation. Alternatively, such end of the cavity can be provided with a post illustrated by broken line and designated 55 in FIG. 2. The post 55 can project into a cavity in the end of the spool providing a shaft for rotation of the spool. Similarly the removable cover 34 has a cavity designated 54A for receiving an end portion of the spool of dental floss. Alternative to such recess 54A, a central pin 55 can be provided so as to project into a recess in the end of the spool. The recesses journaling the spool and/or central pins journaling the spool provide for smooth rotation of the spool of floss reducing the tendency of the floss to tangle while being dispensed from the spool.

In the embodiment illustrated in FIG. 4, the dental floss spool 33A fits into a vertically disposed cavity designated 32A.

Access to the cavity is provided by a screw in plug 34A threaded into an aperture in the bottom wall 37A of the housing. In the embodiment illustrated in FIG. 4, the dove tail groove 22A is located in the back wall 53 of the housing and is adapted to receive a correspondingly shaped dove tail flange on a mounting base attachable in any convenient manner to a base structure such as a mirror in a bathroom.

The base 20 and body 31 of the dental floss dispenser are preferably molded from a plastics material, but may be made of wood or any other suitable material. The body is illustrated as being generally rectangular, but by way of example and with reference to FIG. 1, side walls 35 and 36 instead of being parallel to one another can slope, for example upwardly and inwardly in a direction toward one another merging into an apex at the top wall. Alternatively the top wall, instead of being in a flat plane can be curved so as to provide a domed or rounded top. The main feature to all embodiments is that the cutting edge 51 of the cutting knife is located below the top wall 38 of the body member.

Property of privilege is claimed are defined as follows:

1. A floss dispenser comprising:
   a. a body having a cavity for holding a spool of dental floss;
   b. a cover removably mounted on said body providing access to the cavity for replacing a spent spool of dental floss;
   c. an outlet hole in the body member for pulling therethrough a string of dental floss on a spool in the cavity;
   d. a series of side-by-side slots in walls of the body and extending from one side wall to the other; and
   e. a blade located within said body and having a longitudinal cutting edge exposed in respective ones of said slots.

2. A dental floss dispenser as defined in claim 1 wherein said cutting edge is spaced downwardly from an upper edge of the body member.

3. A dental floss dispenser as defined in claim 1 wherein said grooves extend from one to the other of a pair of opposite side walls and across the top wall and wherein the cutting edge of the blade is located at a position spaced downwardly from said top wall.

4. A dental floss dispenser as defined in claim 1 including a mounting base detachably connected to the body of the dispenser.

5. A dental floss dispenser as defined in claim 1 wherein the cavity for the spool of dental floss has means therein for journaling a spool of dental floss for rotation.

6. A dispenser as defined in claim 5 wherein said cover comprises a cap member at least partially insertable into an aperture into a wall of the body.

* * * * *